(12) United States Patent
Georgeson et al.

(10) Patent No.: US 9,316,512 B2
(45) Date of Patent: Apr. 19, 2016

(54) NONDESTRUCTIVE INSPECTION SYSTEM FOR DIFFICULT TO ACCESS AREAS

(71) Applicant: The Boeing Company, Chicago, IL (US)

(72) Inventors: Gary Ernest Georgeson, Tacoma, WA (US); James J. Troy, Issaquah, WA (US); Nathan Rylan Smith, St. Charles, MO (US); Donald Duane Palmer, Jr., Ballwin, MO (US)

(73) Assignee: THE BOEING COMPANY, Chicago, IL (US)

( * ) Notice: Subject to any disclaimer, the term of this patent is extended or adjusted under 35 U.S.C. 154(b) by 373 days.

(21) Appl. No.: 13/915,121

(22) Filed: Jun. 11, 2013

(65) Prior Publication Data

US 2014/0360289 A1    Dec. 11, 2014

(51) Int. Cl.
| | |
|---|---|
| *G01D 11/30* | (2006.01) |
| *G01N 29/22* | (2006.01) |
| *G01N 29/265* | (2006.01) |
| *G01N 21/954* | (2006.01) |
| *G01N 27/90* | (2006.01) |

(52) U.S. Cl.
CPC .............. *G01D 11/30* (2013.01); *G01N 21/954* (2013.01); *G01N 29/225* (2013.01); *G01N 29/265* (2013.01); *G01N 27/902* (2013.01); *G01N 2291/2638* (2013.01); *G01N 2291/2694* (2013.01)

(58) Field of Classification Search
CPC ....................................................... G01R 33/12
USPC .......................................... 73/865.8; 324/219
See application file for complete search history.

(56) References Cited

U.S. PATENT DOCUMENTS

| | | | |
|---|---|---|---|
| 4,139,822 | A | 2/1979 | Urich et al. |
| 8,109,160 | B2 | 2/2012 | Bossi et al. |
| 2011/0018530 | A1* | 1/2011 | Bousquet et al. ............ 324/240 |

OTHER PUBLICATIONS

International Search Report and Written Opinion, dated Aug. 4, 2014, regarding Application No. PCT/US2014/031571, 9 pages.
Rutherford et al., "Sensor Coupling Apparatus," U.S. Appl. No. 13/547,190, filed Jul. 12, 2012, 25 pages.
"Remote Visual Inspection—Industrial Videoscopes, Industrial Fiberscope, Borescope—Olympus," Olympus Corporation, copyright 2013, 2 pages, accessed Jun. 11, 2013. www.olympus-ims.com/en/rvi-products/.
Georgeson et al., "Surgical NDE (SuNDE) Tool for Limited Access Inspection," The Boeing Company, ASNT Fall Conference, Oct. 2011, 35 pages.

* cited by examiner

*Primary Examiner* — Peter Macchiarolo
*Assistant Examiner* — Anthony W Megna Fuentes
(74) *Attorney, Agent, or Firm* — Yee & Associates, P.C.

(57) ABSTRACT

A method for inspecting an object. A support structure physically associated with a first sensor and a second sensor is moved to an area for inspection. The support structure is in a first configuration and the first sensor and the second sensor are positioned about an axis extending through the support structure when the support structure is in the first configuration. The support structure is changed from the first configuration to a second configuration. The first sensor and the second sensor are configured to generate information when the support structure is in the second configuration.

20 Claims, 13 Drawing Sheets

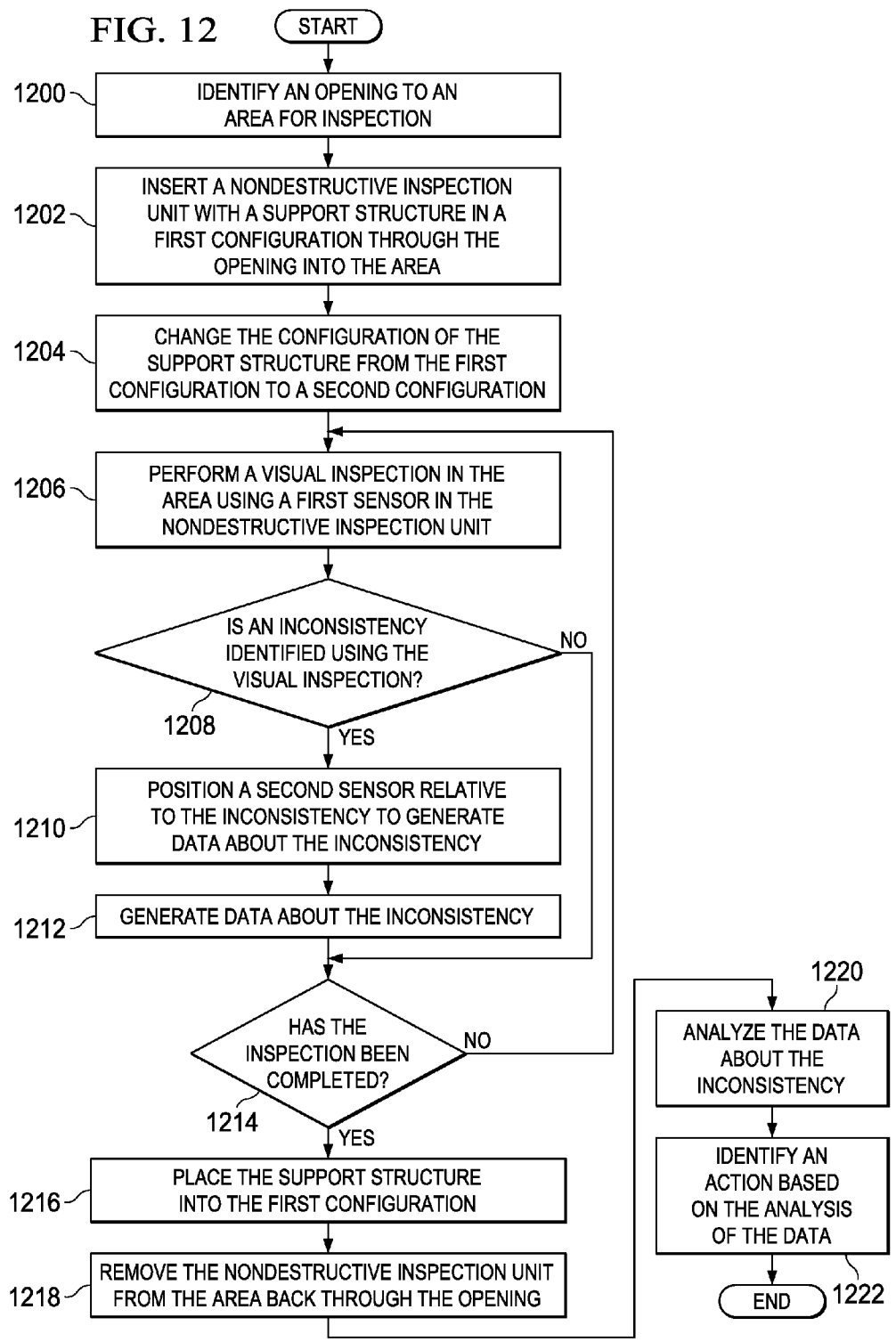

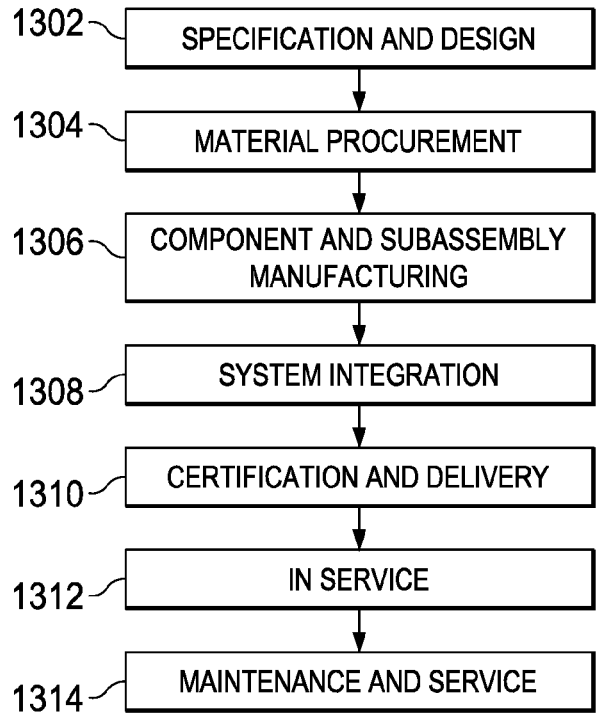
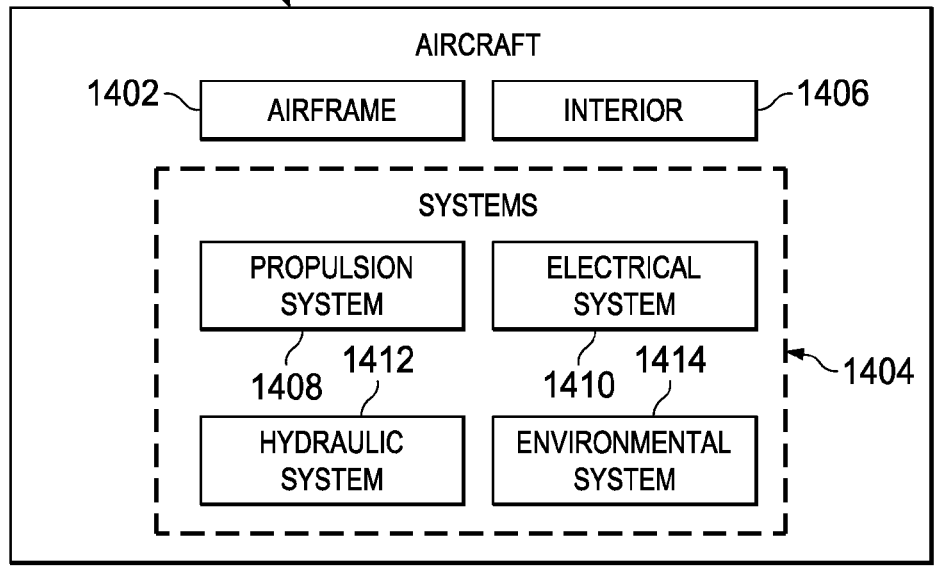

NONDESTRUCTIVE INSPECTION SYSTEM FOR DIFFICULT TO ACCESS AREAS

BACKGROUND INFORMATION

1. Field

The present disclosure relates generally to inspecting objects and, in particular, to performing nondestructive inspection of objects. Still more particularly, the present disclosure relates to a method and apparatus for nondestructive inspection in locations that are difficult to access.

2. Background

In manufacturing aircraft, vehicles, and other structures, inspection of parts used to form these structures is often performed to determine whether the parts will have desired parameters for a desired performance of the part. Nondestructive testing is commonly performed on these parts. Nondestructive testing is used to evaluate properties of a part without altering the ability of the part to be employed in service. Nondestructive testing may include ultrasound testing, eddy current testing, x-ray testing, visual inspections, and other types of testing.

This type of testing may also be performed after the object has been manufactured. Inspections may be performed while an object is in use to determine whether the object still performs as desired. The inspection may be performed during maintenance or other times to determine whether inconsistencies may be present that may require maintenance, rework, replacement, or some combination thereof.

When inspecting an object, such as an aircraft, a visual inspection may be first made to see if any inconsistencies may be present. An operator may view different areas of the aircraft to determine whether an inconsistency is present that may require an additional inspection.

If an inconsistency is identified in an area of the aircraft through the visual inspection, the nondestructive inspection may be performed to generate information that may be analyzed. For example, the inspection may be performed using an eddy current sensor, an ultrasonic sensor, or some other suitable type of device. The information generated from this inspection may be used to determine the extent of the inconsistency, the depth of the inconsistency, and other information about the inconsistency. With this information, a determination may be made as to what actions may be taken such as increased inspections of the area, rework of the area, replacement of the part, or other suitable actions.

Performing visual inspections and additional nondestructive inspections may be more difficult than desired. Some areas of the aircraft may be difficult to reach. For example, an interior of a wing, a fuel tank, and other areas in the aircraft may be difficult to reach because of the amount of access for using existing types of nondestructive inspection devices.

In some cases, disassembly of a portion of the aircraft may be performed to reach areas for inspection. The disassembly and reassembly of a portion of the aircraft may take more time and effort than desired. As a result, maintenance for an aircraft may be more expensive than desired. Additionally, the aircraft also may be out of service for longer periods than desired to perform needed inspections.

Therefore, it would be desirable to have a method and apparatus that takes into account at least some of the issues discussed above, as well as other possible issues.

SUMMARY

In one illustrative embodiment, an apparatus comprises a sensor, a tool, and a support structure. The support structure is physically associated with the sensor and the tool. The support structure is configured to change between a first configuration and a second configuration. The support structure with the sensor and the tool are configured to move through an opening in an object when the support structure is in the first configuration.

In another illustrative embodiment, a nondestructive inspection system comprises a borescope, a sensor, and a support structure. The support structure is physically associated with the borescope and the sensor. The borescope and the sensor are positioned about an axis extending through the support structure when the support structure is in a first configuration. The support structure is configured to change between the first configuration and a second configuration. The support structure with the borescope and the sensor are configured to move through an opening in a structure when the support structure is in the first configuration. The borescope and the sensor are configured to generate information when the support structure is in the second configuration.

In yet another illustrative embodiment, a method for inspecting an object is presented. A support structure physically associated with a first sensor and a second sensor is moved to an area for inspection. The support structure is in a first configuration and the first sensor and the second sensor are positioned about an axis extending through the support structure when the support structure is in the first configuration. The support structure is changed from the first configuration to a second configuration. The first sensor and the second sensor are configured to generate information when the support structure is in the second configuration.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 12 is an illustration of a flowchart of a process for inspecting a difficult to access area in accordance with an illustrative embodiment;

FIG. 13 is an illustration of an aircraft manufacturing and service method in the form of a block diagram in accordance with an illustrative embodiment; and FIG. 14 is an illustration of an aircraft in the form of a block diagram in which an illustrative embodiment may be implemented.

DETAILED DESCRIPTION

Figure 1:
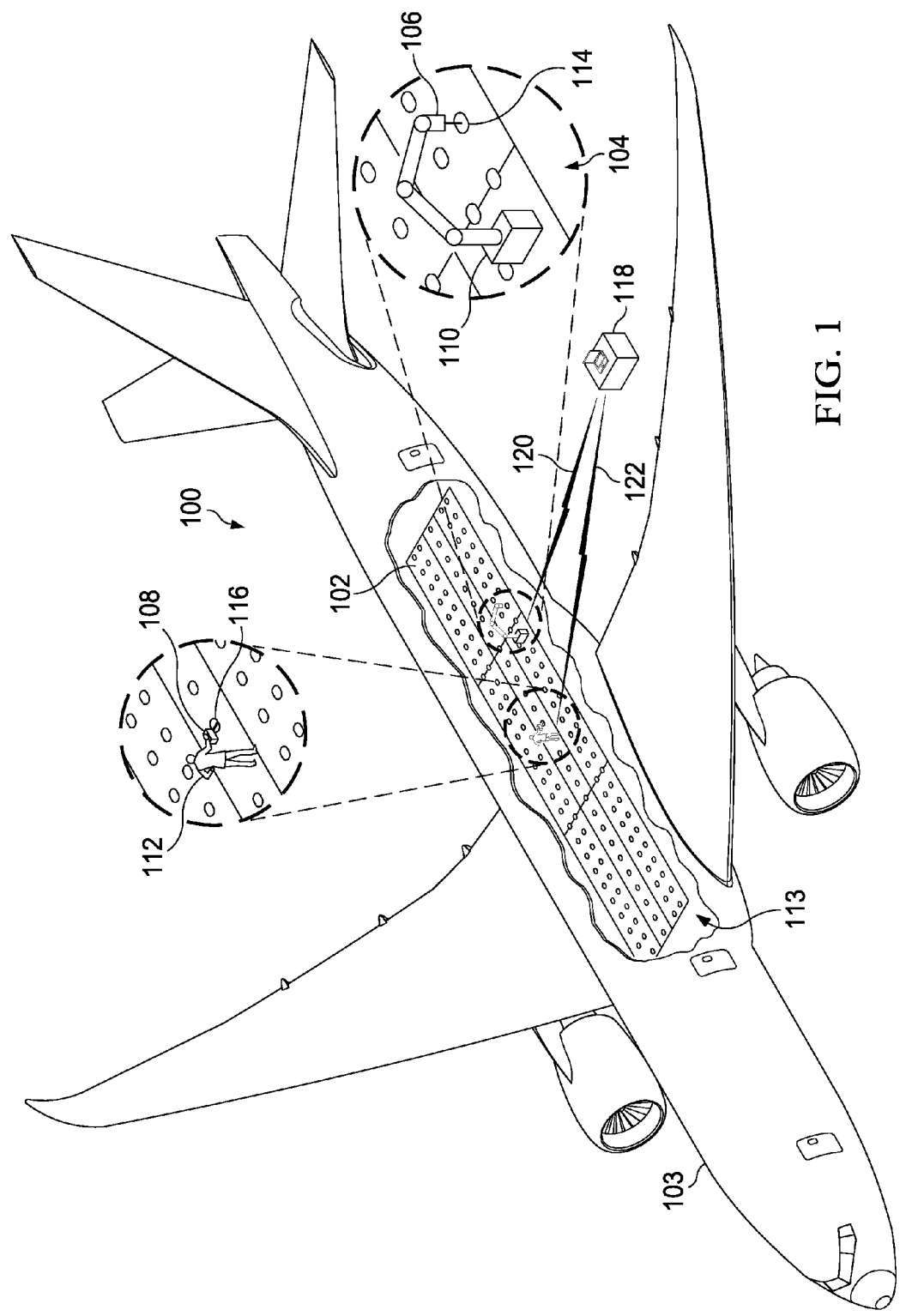
FIG. 1 is an illustration of an inspection environment in accordance with an illustrative embodiment.

The illustrative embodiments recognize and take into account different considerations. For example, the illustrative embodiments recognize and take into account that visual inspections may be made using an imaging sensor camera. For example, a borescope may be used to inspect areas that may not be easily accessible or reviewable by a human operator. A borescope is an optical device that has a tube. The tube may be rigid, flexible or both. One end has a lens and the other end has an eye piece or an imaging system. An operator may use this device to perform a visual inspection of the aircraft. A borescope may be placed through openings to reach an area that may be hard to view without disassembling a portion of the aircraft. In this manner, the illustrative embodiments recognize and take into account that an operator may need a better ability to perform a visual inspection of an interior area such as a fuel tank or the interior of a wing.

Illustrative embodiments also recognize and take into account that when an additional inspection is needed, another sensor may be inserted into the area. The borescope may be used by the operator to view the area and to guide the second sensor to the area for performing an additional inspection to generate information about the inconsistency for analysis.

The illustrative embodiments recognize and take into account that in some cases, the opening may not be sufficient in size to allow the entry of both the borescope and the other sensor at the same time. As a result, an operator may be unable to see to direct the second sensor to the area to generate information. In this case, a search for an additional opening to access the area is needed. In some cases, an additional opening is not present without forming that additional opening. As a result, disassembly of a portion of the aircraft may be needed to perform the additional inspection of the area in the aircraft.

Thus, the illustrative embodiments apply to a method and apparatus for inspecting an area for an object. Although the illustrative embodiments may be applied to any area for the object, the illustrative embodiments may also be applied to areas that may be difficult to access.

For example, a support structure physically associated with the first sensor and the second sensor in a first configuration may be moved to an area for inspection. The first sensor and the second sensor are positioned about an axis extending through the support structure when the support structure is in the first configuration. The support structure may be changed from the first configuration to a second configuration. The first sensor and the second sensor are configured to generate information when the support structure is in the second configuration.

In the second configuration, the movement of the support structure may be guided using first information in the information generated by the first sensor to guide the support structure to a position relative to the area for inspection. Second information in the information may be generated with the second sensor when the second sensor is in the desired position relative to the area for inspection.

With reference now to the figures, and in particular, with reference to FIG. 1, an illustration of an inspection environment is depicted in accordance with an illustrative embodiment. In this illustrative example, inspection environment 100 is an environment in which nondestructive inspections may be performed.

As depicted, cargo floor panel 102 is seen in this exposed view in aircraft 103 in inspection environment 100. Cargo floor panel 102 is an example of an object that may be inspected with nondestructive inspection system 104. In this illustrative example, this inspection may be performed using nondestructive inspection unit 106 and nondestructive inspection unit 108 in nondestructive inspection system 104.

Nondestructive inspection unit 106 is operated by robot 110. Nondestructive inspection unit 108 is operated by human operator 112. In particular, the inspection performed using nondestructive inspection unit 106 and nondestructive inspection unit 108 may be in interior 113 of aircraft 103 under cargo floor panel 102.

As depicted, nondestructive inspection unit 106 is configured to reach interior 113 of aircraft 103 under cargo floor panel 102 through opening 114. In this illustrative example, nondestructive inspection unit 106 may have a first configuration for moving through opening 114. Nondestructive inspection unit 106 may then change to a second configuration for performing the inspection in interior 113.

In a similar fashion, nondestructive inspection unit 108 is configured to reach interior 113 of aircraft 103 through opening 116 in cargo floor panel 102. Nondestructive inspection unit 108 also has a first configuration. This first configuration is used when moving nondestructive inspection unit 108 through opening 116 in cargo floor panel 102. Nondestructive inspection unit 108 then changes into a second configuration when performing the inspection of interior 113.

In these illustrative examples, opening 114 and opening 116 may have a size that does not allow nondestructive inspection unit 106 and nondestructive inspection unit 108 to pass through opening 114 and opening 116 when these nondestructive inspection units are in the second configuration. In these illustrative examples, opening 114 and opening 116 are fastener holes.

As depicted, nondestructive inspection unit 106 may generate and send information to computer 118 over wireless communications link 120. In a similar fashion, nondestructive inspection unit 108 also may send information to computer 118 over wireless communications link 122. This information may be analyzed to determine whether inconsistencies are present in cargo floor panel 102 and what actions should be taken if inconsistencies are detected in cargo floor panel 102.

The illustration of inspection environment 100 is provided as one example of an implementation for an inspection environment. Of course, other inspection environments may include other types of objects and numbers of objects for inspection. Additionally, other numbers of nondestructive inspection units may be present in other illustrative examples.

Figure 2:
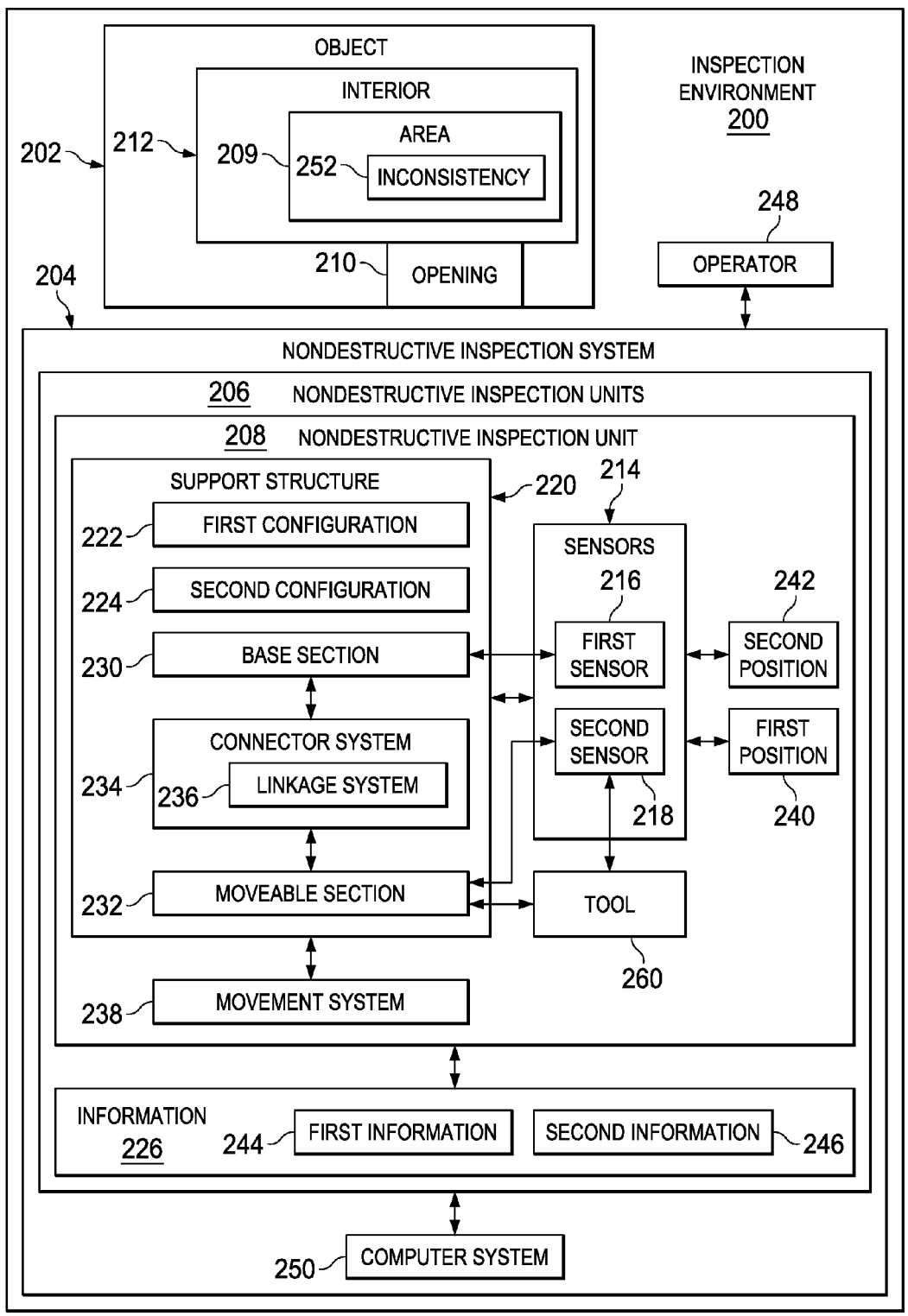
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. Inspection environment 100 in FIG. 1 is an example of one implementation for inspection environment 200 shown in block form in FIG. 2.

As depicted, object 202 may be inspected in inspection environment 200 using nondestructive inspection system 204. Object 202 may take various forms. For example, object 202 may be cargo floor panel 102 in FIG. 1. Further, object 202 may be selected from various types of objects. For example, object 202 may be selected from one of a mobile platform, a stationary platform, a land-based structure, an aquatic-based structure, a space-based structure, a deformable structure, a flexible fuel bag, a fuel line, a surface ship, a tank, a personnel carrier, a train, a spacecraft, a space station, a satellite, a submarine, an automobile, a power plant, a bridge, a dam, a house, a manufacturing facility, a building, a fairing, a fuel tank, a fuselage, an engine, and a duct system.

Nondestructive inspection system 204 includes a group of nondestructive inspection units 206. As used herein, a "group of," when used with reference to items, means one or more items. For example, a group of nondestructive inspection units 206 is one or more nondestructive inspection units.

In the illustrative examples, nondestructive inspection unit 208 within the group of nondestructive inspection units 206 is used to perform an inspection of object 202. As depicted, nondestructive inspection unit 208 may be moved to area 209 for inspection of object 202. For example, nondestructive inspection unit 208 may be configured to move through opening 210 into interior 212 of object 202 to perform an inspection of interior 212 of object 202. Opening 210 may take various forms. For example, opening 210 may be a fastener hole, a slot, an access port, a gap between parts, or some other suitable type of opening.

As depicted, nondestructive inspection unit 208 includes sensors 214. In this illustrative example, sensors 214 comprise first sensor 216 and second sensor 218. Sensors 214 may be implemented using any sensor desired for performing an inspection of object 202. For example, first sensor 216 may be selected from one of a camera, a video imaging system, a borescope, and other suitable types of sensors. As another illustrative example, second sensor 218 may be selected from one of an eddy current sensor, an ultrasonic transducer, a chemical sensor, a biological sensor, an infrared sensor, a thermocouple temperature sensor, a magnetic field sensor, a vibration sensor, an electrical potential sensor, an electrostatic discharge (ESD) sensor and other suitable types of sensors.

Nondestructive inspection unit 208 also includes support structure 220. Sensors 214 are physically associated with support structure 220. In particular, first sensor 216 and second sensor 218 are physically associated with support structure 220.

When one component is "physically associated" with another component, the association is a physical association in the depicted examples. For example, a first component, first sensor 216, may be considered to be physically associated with a second component, support structure 220, by being secured to the second component, bonded to the second component, mounted to the second component, welded to the second component, fastened to the second component, and/or connected to the second component in some other suitable manner. The first component also may be connected to the second component using a third component. The first component may also be considered to be physically associated with the second component by being formed as part of the second component, extension of the second component, or both.

In the illustrative example, support structure 220 is configured to change between first configuration 222 and second configuration 224. Support structure 220, with first sensor 216 and second sensor 218, is configured to move through opening 210 when support structure 220 is in first configuration 222. Support structure 220 may take various forms. Support structure 220 may be any type of structure configured to hold sensors 214.

Further, support structure 220 may be comprised of multiple parts. The different parts may be comprised of various materials. For example, the different parts may be comprised of one or more materials that may be selected from at least one of a metal, aluminum, steel, a composite material, plastic, polycarbonate, or other suitable types of materials. Further, some of the parts may be rigid while other parts may be flexible, depending on the particular implementation.

As used herein, the phrase "at least one of," when used with a list of items, means different combinations of one or more of the listed items may be used and only one of each item in the list may be needed. For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A, one of item B, and ten of item C; four of item B and seven of item C; and other suitable combinations. The item may be a particular object, thing, or a category. In other words, at least one of means any combination of items and number of items may be used from the list but not all of the items in the list are required.

For example, support structure 220 may have base section 230 and moveable section 232. Moveable section 232 may move relative to base section 230 in this depicted example. Base section 230 and moveable section 232 may be connected to each other by connector system 234. Connector system 234 may be, for example, linkage system 236. Linkage system 236 comprises one or more structures that facilitate movement of moveable section 232 relative to base section 230. This movement may be at least one of rotational movement, translational movement, or other suitable types of movement.

Connector system 234 is configured to facilitate movement of moveable section 232 relative to base section 230 such that second sensor 218 moves relative to first sensor 216 when support structure 220 moves between first configuration 222 and second configuration 224.

In the illustrative example, movement of support structure 220 between first configuration 222 and second configuration 224 may be performed using movement system 238. Movement system 238 may take various forms. For example, movement system 238 may be selected from at least one of a cable, an actuator, a motor, or some other suitable type of device.

As depicted, first sensor 216 and second sensor 218 are in first position 240 relative to each other when support structure 220 is in first configuration 222. For example, second sensor 218 may be located in front of first sensor 216 in first position 240 when support structure 220 is in first configuration 222. First position 240 of first sensor 216 and second sensor 218 allows for the movement of first sensor 216 and second sensor 218 through opening 210.

After first sensor 216 and second sensor 218 with support structure 220 move through opening 210 into interior 212 of object 202, support structure 220 may change into second configuration 224. This configuration results in first sensor 216 and second sensor 218 having second position 242 relative to each other.

First sensor 216 and second sensor 218 are configured to generate information 226 when support structure 220 is in second configuration 224. For example, first sensor 216 generates first information 244 in information 226. Second sensor 218 generates second information 246 in information 226. For example, first information 244 may be an image or light that may be viewed by operator 248. Second information 246 may be data characterizing object 202. This data may be, for example, readings from eddy currents, a response to ultrasonic signals, or other types of data.

In second configuration 224, first sensor 216 and second sensor 218 in second position 242 are both in a position such that first sensor 216 and second sensor 218 are configured to generate information 226 in a desired manner.

In this illustrative example, first sensor 216 does not move while second sensor 218 moves when support structure 220 changes between first configuration 222 and second configuration 224. In first position 240, second sensor 218 may block first sensor 216 from generating first information 244. In other illustrative examples, second sensor 218 may not be positioned in a position to generate second information 246 when in first position 240. Movement of second sensor 218 into second position 242 is one in which first sensor 216 and second sensor 218 generate information 226 in a desired manner when support structure 220 is in second configuration 224. In other illustrative examples, first sensor 216, second sensor 218, or both sensors may move.

As depicted, at least one of first information 244 and second information 246 in information 226 may be sent to computer system 250. Computer system 250 may be used to analyze this information to determine whether inconsistency 252 is present or may need additional actions.

In this manner, nondestructive inspection unit 208 may be moved to area 209 on object 202 to perform an inspection of object 202. In these illustrative examples, nondestructive inspection unit 208 may be used when area 209 is difficult to reach. For example, when area 209 is located within interior 212 of object 202, access to area 209 may be more difficult than desired. In these illustrative examples, support structure 220 may be changed between first configuration 222 and second configuration 224 to reach area 209. As described above, support structure 220 with first sensor 216 and second sensor 218 may be moved through opening 210 to reach area 209 when in first configuration 222. Then, support structure 220 may be changed to second configuration 224 such that both first sensor 216 and second sensor 218 may generate information 226 in a desired manner.

Further, with the use of nondestructive inspection unit 208, first sensor 216 and second sensor 218 may both be moved through opening 210. As a result, another opening is not needed to move and position both first sensor 216 and second sensor 218 in area 209 to perform inspection of area 209. This type of inspection unit may aid operator 248 when operator 248 uses first sensor 216 to guide second sensor 218 within area 209 to perform an inspection using second sensor 218.

For example, first sensor 216 may be a borescope while second sensor 218 may be an eddy current sensor. Operator 248 may use the borescope to guide movement of support structure 220 such that the eddy current sensor may be used to generate data about a particular portion of area 209.

The illustration of inspection environment 200 shown in block form in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, computer system 250 may be a separate component from nondestructive inspection system 204 in some illustrative examples. As another example, nondestructive inspection unit 208 may be mounted on a robotic arm. In other words, nondestructive inspection unit 208 may be an end effector for a robot. In other illustrative examples, nondestructive inspection unit 208 may be attached to a cable, a rod, or some other suitable structure.

Although nondestructive inspection unit 208 has been described with respect to a first sensor and a second sensor, one or more sensors may be included in nondestructive inspection unit 208 in addition to first sensor 216 and second sensor 218. Additional moveable sections also may be present in addition to moveable section 232.

Other components such as wires, optical fibers, and other communications links may be present that connect nondestructive inspection unit 208 to computer system 250. As another example, nondestructive inspection unit 208 may include a wireless communications unit configured to establish a wireless communications link with computer system 250.

In another illustrative example, second sensor 218 is an example of tool 260. Of course, tool 260 may take other forms other than second sensor 218. For example, tool 260 may be selected from one of a marking instrument, a light, a pen, a marker, a sealant applicator, a paint applicator, and other suitable types of tools. As depicted, tool 260 may be modular. In other words, tool 260 may be removable from moveable section 232 such that another tool may be added in place of tool 260.

For example, when tool 260 takes the form of a marking instrument, tool 260 may be used to mark a location where inconsistency 252 may be seen. As a result, inconsistency 252 may be more easily located in a subsequent inspection.

As another example, when tool 260 takes the form of a marking instrument, indications may be made that identify areas such as area 209 where an inspection has been performed. As a result, when many features of the same type are present, an identification of which features have been inspected may be more easily made. For example, a marking tool may be used to mark fasteners in a long row of fasteners as inspection of the fasteners is performed.

Figure 3:
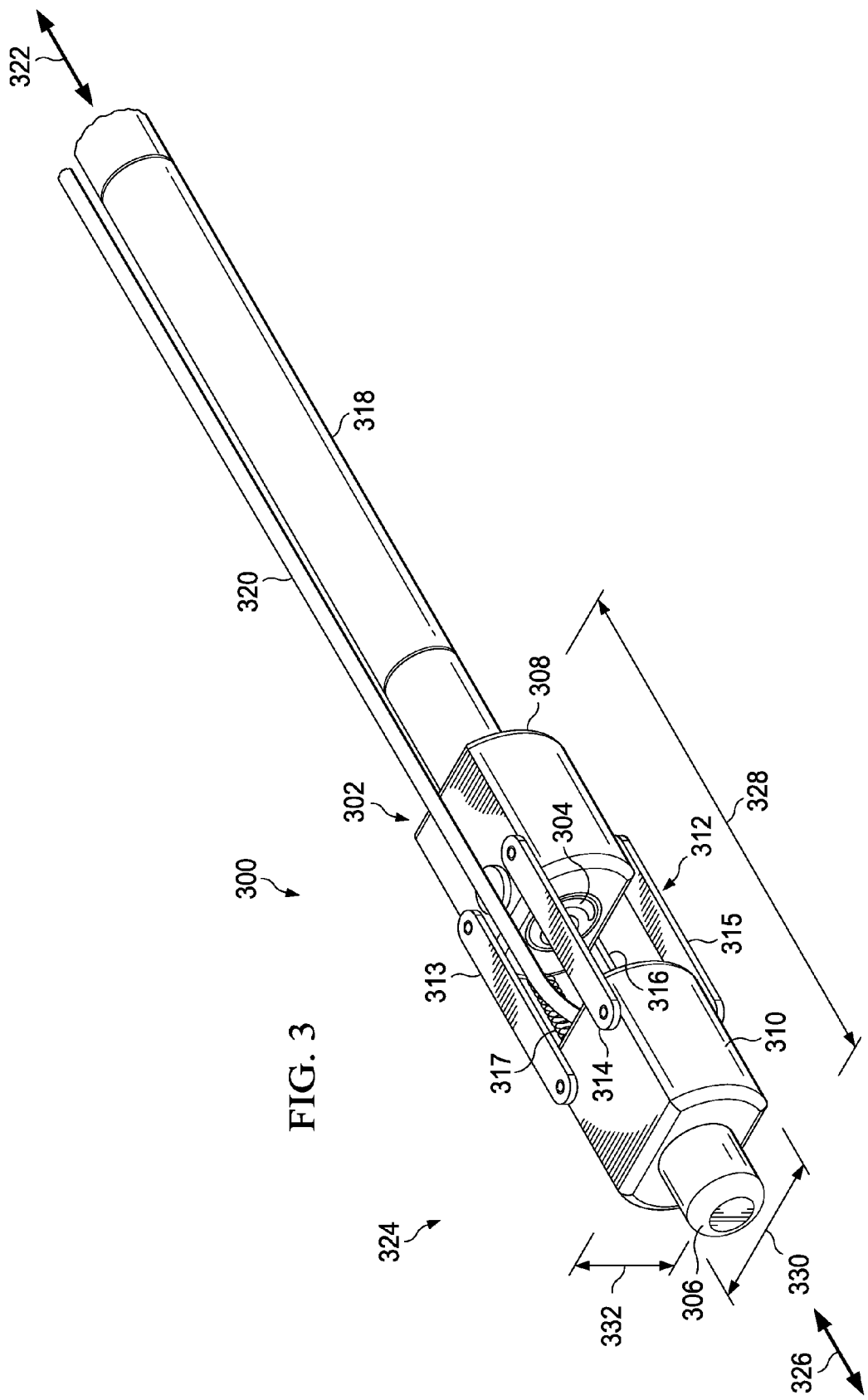
FIG. 3 is an illustration of a nondestructive inspection unit with a support structure in a first configuration in accordance with an illustrative embodiment.

With reference now to FIG. 3, an illustration of a nondestructive inspection unit with a support structure in a first configuration is depicted in accordance with an illustrative embodiment. In this illustrative example, nondestructive inspection unit 300 is an example of a physical implementation for nondestructive inspection unit 208 shown in block form in FIG. 2.

As depicted, nondestructive inspection unit 300 includes support structure 302, borescope 304, and eddy current sensor 306. Borescope 304 is an example of an implementation for first sensor 216 shown in block form in FIG. 2. Eddy current sensor 306 is an example of an implementation for second sensor 218 shown in block form in FIG. 2. Support structure 302 is physically associated with borescope 304 and eddy current sensor 306.

Support structure 302 is comprised of base section 308 and moveable section 310. Borescope 304 is physically associated with base section 308 and eddy current sensor 306 is physically associated with moveable section 310. Base section 308 and moveable section 310 are connected to each other through links 312. Links 312 is an example of an implementation for connector system 234 shown in block form in FIG. 2. In particular, links 312 are an example of an implementation for linkage system 236 shown in block form in FIG. 2. Links 312 includes link 313, link 314, link 315, and link 316. Spring 317 also connects base section 308 to moveable section 310.

As depicted, base section 308 is connected to elongate structure 318. Elongate structure 318 may be manipulated by an operator such as a human operator or a robotic arm to move support structure 302.

Elongate structure 318 may take various forms. For example, elongate structure 318 may be a rod, a cable, or some other suitable structure. Elongate structure 318 may be rigid, flexible, or may have rigid and flexible sections. Further, elongate structure 318 may have features that allow for manipulation of the shape of elongate structure 318. For example, these features may include actuators or cables (not shown). In the illustrative example, the actuators or cables are controlled from the proximal end of support structure 220 or other location on nondestructive inspection unit 208 exterior to the inspection area.

Additionally, cable 320 is also present and may be used to change the configuration of support structure 302. In this illustrative example, cable 320 is configured to provide for force transmission. As depicted, cable 320 is connected to moveable section 310. Cable 320 may be manipulated by an operator to cause movement of moveable section 310 relative to base section 308. In this illustrative example, the manipulation may be a force that may push or pull cable 320 in the direction of arrow 322. Cable 320 may be attached to a locking mechanism (not shown) that allows moveable section 310 to maintain a selected position. Additionally, cable 320 also may include one or more wires for operating eddy current sensor 306.

In this illustrative example, nondestructive inspection unit 300 is in first configuration 324. In particular, spring 317 biases moveable section 310 and base section 308 to first configuration 324.

In first configuration 324, borescope 304 and eddy current sensor 306 are positioned about axis 326 extending through support structure 302 when support structure 302 is in first configuration 324. In this particular example, axis 326 also extends centrally through borescope 304 and eddy current sensor 306.

In this configuration, eddy current sensor 306 and borescope 304 are in a first position relative to each other. In this first position, eddy current sensor 306 is located in front of borescope 304. With this positioning, eddy current sensor 306 and borescope 304 are considered to be in line with each other.

As a result, an operator may be unable to view images as desired when support structure 302 is in first configuration 324. However, this configuration allows for nondestructive inspection unit 300 to pass through an opening.

As depicted, support structure 302 with borescope 304 and eddy current sensor 306 has length 328, width 330, and height 332. The values for these dimensions may vary depending on the particular use for nondestructive inspection unit 300.

For example, if support structure 302 in nondestructive inspection unit 300 is designed for entry through fastener holes, length 328 may be about 1.0 inch, width 330 may be about 0.35 inches, and height 332 may be about 0.25 inches. These values may vary depending on the size of the opening, the shape of the opening, or both the size and shape of the opening.

Figure 4:
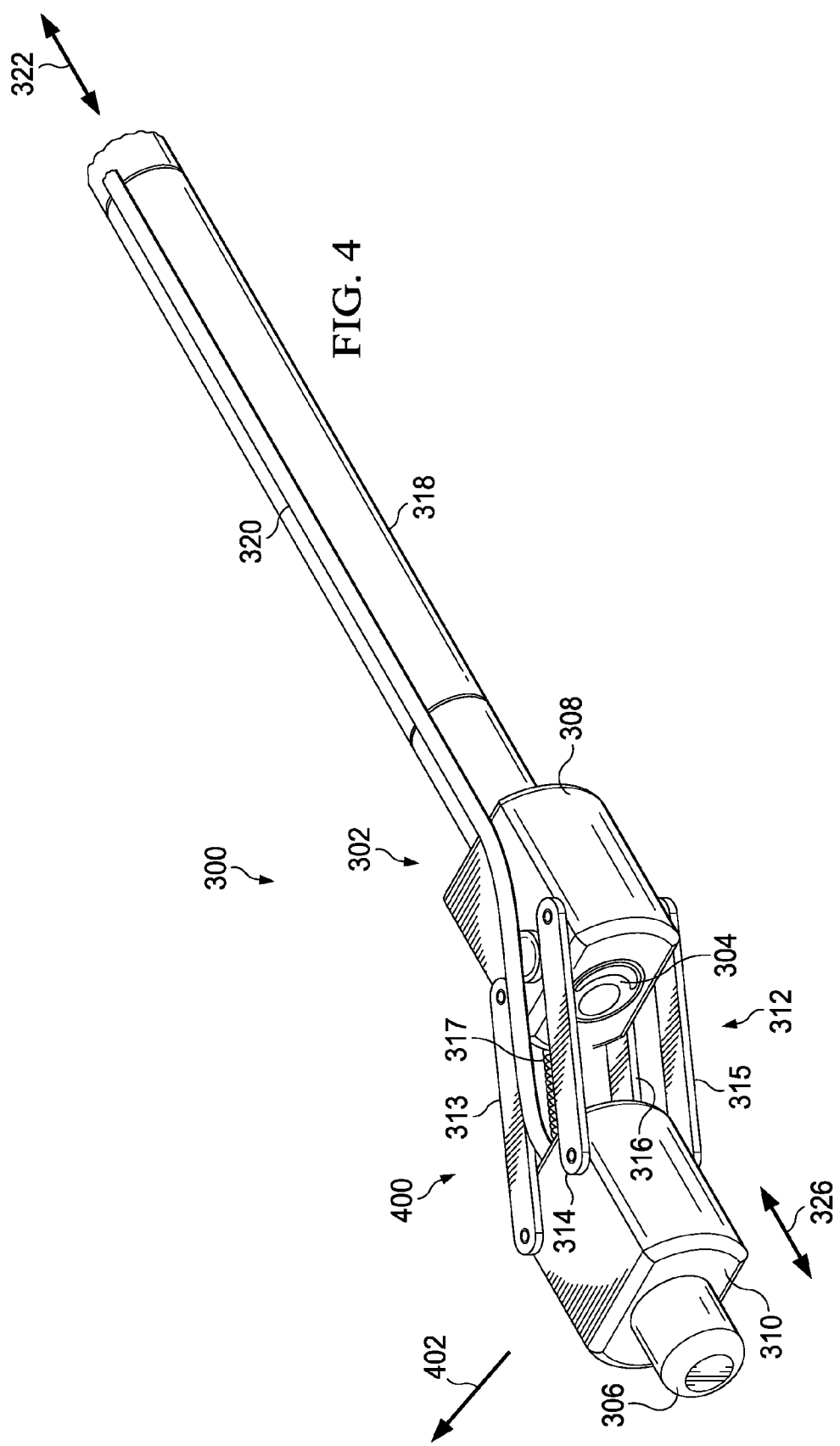
FIG. 4 is an illustration of a nondestructive inspection unit with a support structure in a second configuration in accordance with an illustrative embodiment.

With reference now to FIG. 4, an illustration of a nondestructive inspection unit with a support structure in a second configuration is depicted in accordance with an illustrative embodiment. In this illustrative example, support structure 302 has changed from first configuration 324 as depicted in FIG. 3 to second configuration 400.

As can be seen, moveable section 310 has been moved in the direction of arrow 402 relative to base section 308. In this illustrative example, this movement may be caused through manipulation of cable 320 in the direction of arrow 322.

As a result, eddy current sensor 306 is now in a second position relative to borescope 304. In other words, eddy current sensor 306 has moved laterally with respect to borescope 304. In this position, eddy current sensor 306 has been moved away from axis 326 out of the way of borescope 304. With this positioning, a line of sight is present through borescope 304.

As a result, borescope 304 and eddy current sensor 306 may both generate information in a desired manner. In other words, eddy current sensor 306 and moveable section 310 no longer obscure the view of borescope 304 when support structure 302 is in second configuration 400.

In second configuration 400, borescope 304 may provide a view of an area of an object. This view may be used to guide support structure 302 to a portion of the area such that eddy current sensor 306 may be used to generate data about the area.

For example, in this configuration, borescope 304 may be used by an operator to perform a visual inspection. If the operator sees an inconsistency, the operator may use this view to move support structure 302 in a manner that positions eddy current sensor 306 to generate data about the inconsistency.

In second configuration 400, support structure 302 is unable to pass through an opening. As a result, when the inspection is completed, support structure 302 may be changed back to first configuration 324 as depicted in FIG. 3. In first configuration 324, support structure 302 may be moved back through the opening. In these illustrative examples, spring 317 biases moveable section 310 back into position around axis 326 to return to first configuration 324. This movement may occur when cable 320 is no longer manipulated or released.

Figure 5:
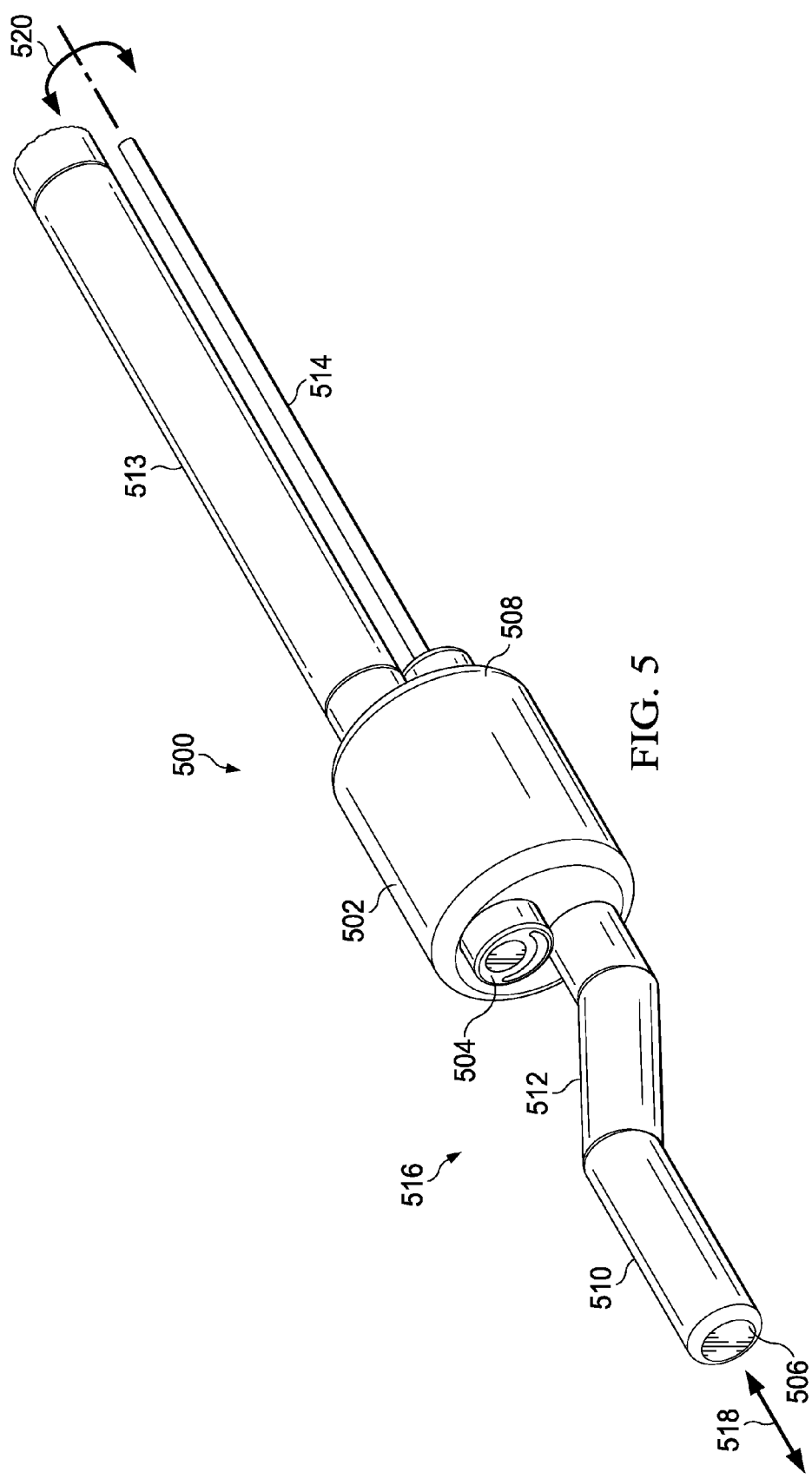
FIG. 5 is an illustration of a nondestructive inspection unit with a support structure in a first configuration in accordance with an illustrative embodiment.

Turning now to FIG. 5, an illustration of a nondestructive inspection unit with a support structure in a first configuration is depicted in accordance with an illustrative embodiment. In this illustrative example, nondestructive inspection unit 500 is another example of nondestructive inspection unit 208 shown in block form in FIG. 2.

As depicted, nondestructive inspection unit 500 includes support structure 502, borescope 504, and eddy current sensor 506. Borescope 504 is an example of an implementation for first sensor 216 shown in block form in FIG. 2. Eddy current sensor 506 is an example of an implementation for second sensor 218 shown in block form in FIG. 2. Support structure 502 is physically associated with borescope 504 and eddy current sensor 506.

Support structure 502 is comprised of base section 508 and moveable section 510. Borescope 504 is physically associated with base section 508 and eddy current sensor 506 is physically associated with moveable section 510. Base section 508 and moveable section 510 are connected to each other through rotating connector 512. Rotating connector 512 is an example of an implementation for connector system 234 shown in block form in FIG. 2. In particular, rotating connector 512 may be an example of an implementation for linkage system 236 shown in block form in FIG. 2.

Additionally, base section 508 is connected to elongate structure 513. Elongate structure 513 may take various forms.

For example, elongate structure 513 may be a rod, a cable, or some other suitable structure. Elongate structure 513 may be rigid, flexible, or may have rigid and flexible sections.

Cable 514 extends through base section 508 and rotating connector 512 to moveable section 510. In this illustrative example, cable 514 also may include wires configured to operate eddy current sensor 506.

As depicted, support structure 502 is in first configuration 516. In this configuration, borescope 504 and eddy current sensor 506 are positioned about axis 518 extending through support structure 502 when support structure 502 is in first configuration 516.

In first configuration 516, support structure 502 with borescope 504 and eddy current sensor 506 may be moved through an opening. As depicted, the position of eddy current sensor 506 and moveable section 510 may obscure a view of borescope 504. In particular, eddy current sensor 506 may be in line with borescope 504.

Cable 514 may be used to cause rotation of moveable section 510 and rotating connector 512 such that eddy current sensor 506 does not obscure the view of borescope 504. Cable 514 may be manipulated by an operator to cause rotation of moveable section 510. In these illustrative examples, cable 514 may be twisted in the direction of arrow 520 to cause this movement of moveable section 510.

Figure 6:
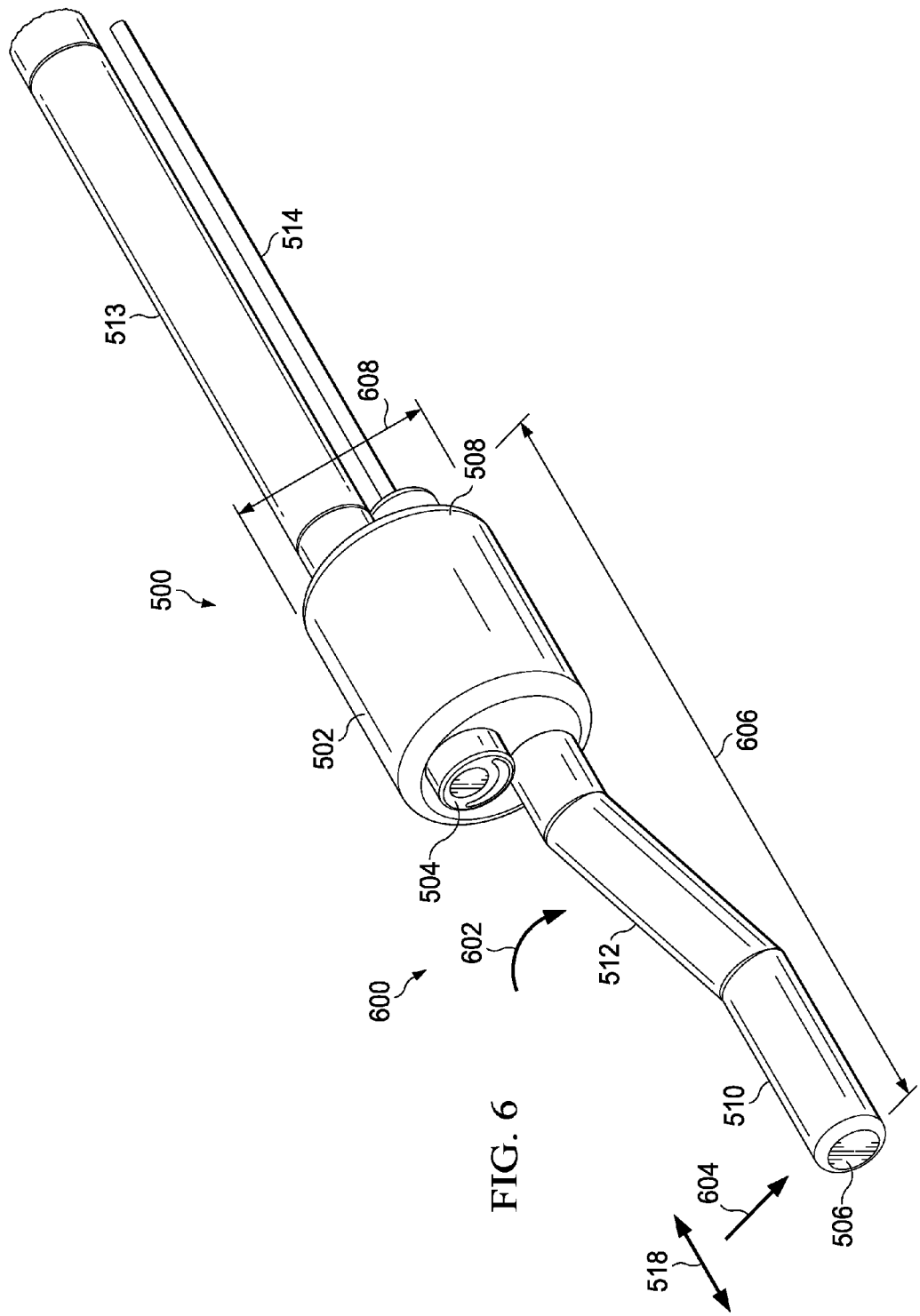
FIG. 6 is an illustration of a nondestructive inspection unit with a support structure in a second configuration in accordance with an illustrative embodiment.

With reference now to FIG. 6, an illustration of a nondestructive inspection unit with a support structure in a second configuration is depicted in accordance with an illustrative embodiment. In this illustrative example, support structure 502 is in second configuration 600.

As depicted, moveable section 510 has been moved in the direction of arrow 602. In this illustrative example, this movement is a rotational movement facilitated by rotating connector 512 and a manipulation of cable 514. In this illustrative example, the rotational movement in the direction of arrow 602 is about 180 degrees. This rotational movement also results in a translation of eddy current sensor 506 away from axis 518 in the direction of arrow 604.

In second configuration 600, eddy current sensor 506 has been moved to a position away from axis 518. In this position, both borescope 504 and eddy current sensor 506 are in positions for generating information in a desired manner when performing an inspection of an object.

When the inspection is completed, moveable section 510 with eddy current sensor 506 may be moved back into its original position such that support structure 502 returns to first configuration 516 as seen in FIG. 5. This movement may be caused by manipulating cable 514. With support structure 502 in first configuration 516, support structure 502 with borescope 504 and eddy current sensor 506 may then be moved back through an opening.

In this illustrative example, support structure 502 may have length 606 and diameter 608. In this illustrative example, length 606 may be about 1.0 inch and diameter 608 may be about 0.35 inches. Of course, these values may vary depending on the opening through which support structure 502 is to be passed.

Figure 7:
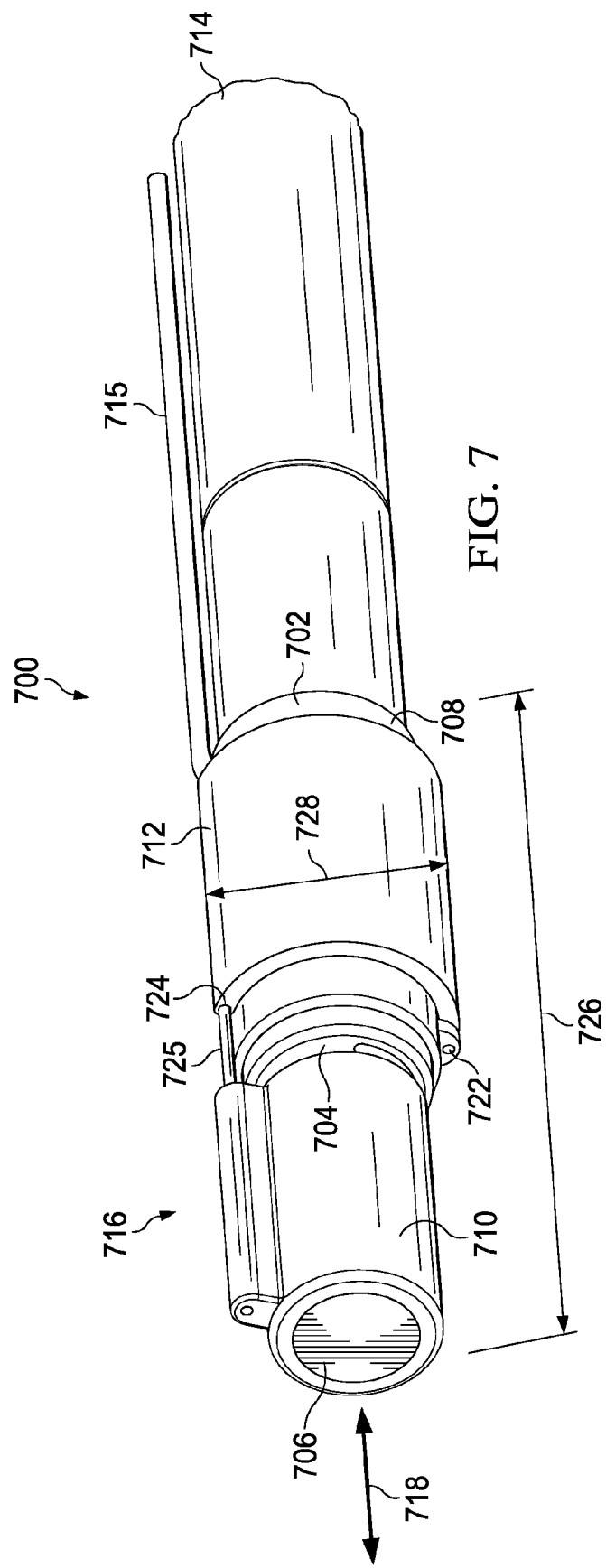
FIG. 7 is an illustration of a nondestructive inspection unit with a support structure in a first configuration in accordance with an illustrative embodiment.

With reference now to FIG. 7, an illustration of a nondestructive inspection unit with a support structure in a first configuration is depicted in accordance with an illustrative embodiment. In this illustrative example, nondestructive inspection unit 700 is another example of nondestructive inspection unit 208 shown in block form in FIG. 2.

As depicted, nondestructive inspection unit 700 includes support structure 702, borescope 704, and eddy current sensor 706. Borescope 704 is an example of an implementation for first sensor 216 shown in block form in FIG. 2. Eddy current sensor 706 is an example of an implementation for second sensor 218 shown in block form in FIG. 2. Support structure 702 is physically associated with borescope 704 and eddy current sensor 706.

Support structure 702 is comprised of base section 708 and moveable section 710. Borescope 704 is physically associated with base section 708 and eddy current sensor 706 is physically associated with moveable section 710. Base section 708 and moveable section 710 are connected to each other through link 712. In this illustrative example, link 712 is an example of an implementation for connector system 234 and, in particular, linkage system 236 shown in block form in FIG. 2.

As depicted, link 712 is connected to base section 708 through hinge 722. Link 712 is connected to moveable section 710 through hinge 724. As a result, link 712 may rotate relative to base section 708 and moveable section 710 may rotate relative to link 712. This rotation may result in a translation of moveable section 710 relative to base section 708.

As depicted, base section 708 is connected to elongate structure 714. Additionally, cable 715 is also present. Cable 715 is connected to moveable section 710 through pin 725 of hinge 724 in this illustrative example.

As depicted, support structure 702 is in first configuration 716. In first configuration 716 of support structure 702, borescope 704 and eddy current sensor 706 are positioned about axis 718 extending through support structure 702 and, in particular, through base section 708 in support structure 702.

As depicted, this position of eddy current sensor 706 relative to borescope 704 may obscure the view of borescope 704. In particular, eddy current sensor 706 and borescope 704 are in line with each other with axis 718 extending centrally through these two sensors. First configuration 716 is used when nondestructive inspection unit 700 is moved through an opening in this illustrative example.

Link 712 and moveable section 710 are rotated out of first configuration 716 to perform an inspection. This movement out of first configuration 716 may be performed by manipulating cable 715.

In this illustrative example, support structure 702 may have length 726 and diameter 728. In this illustrative example, length 726 may be about 1.0 inch and diameter 728 may be about 0.35 inches. Of course, these values may vary depending on the opening through which support structure 702 is to be passed.

Figure 8:
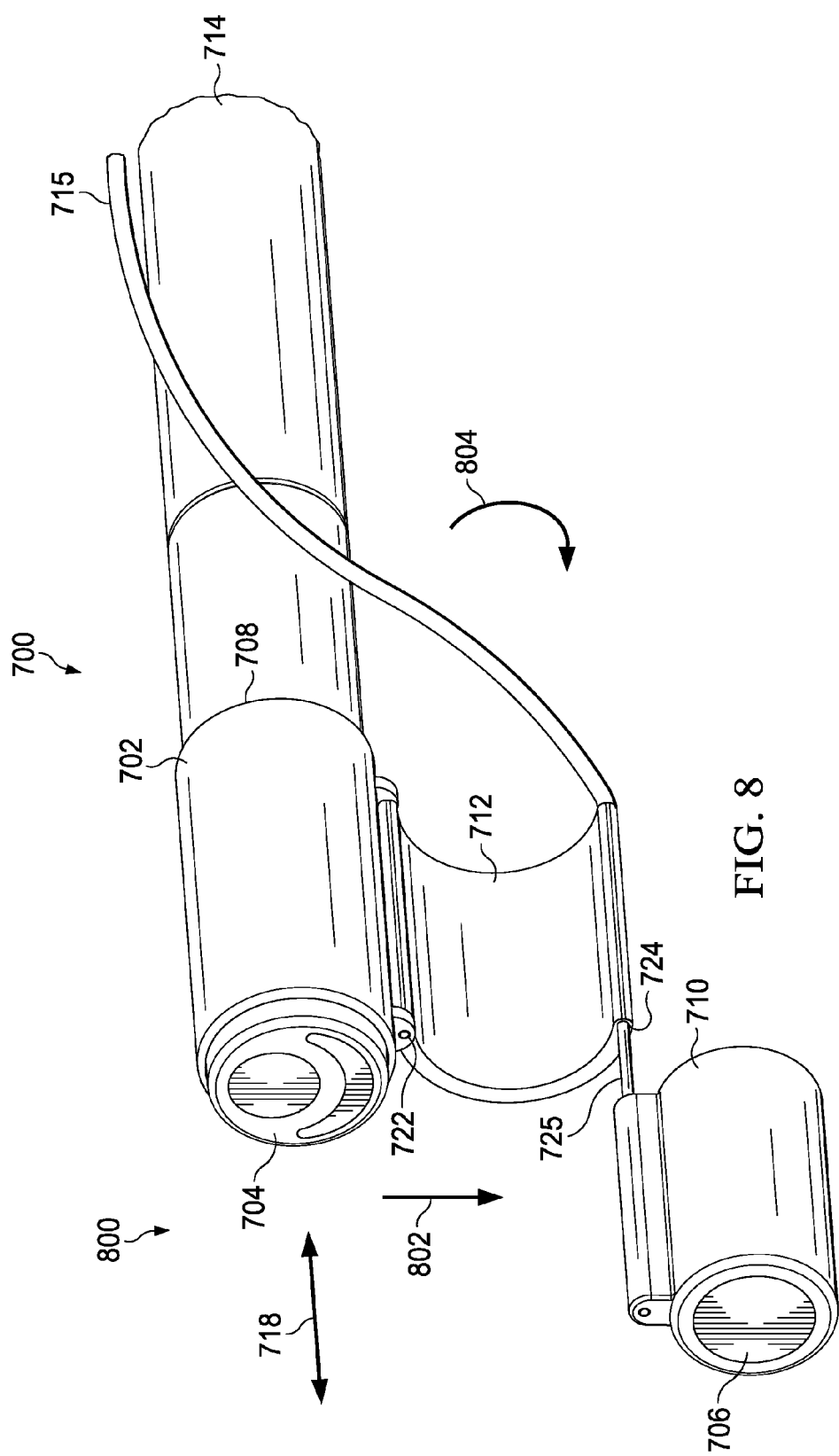
FIG. 8 is an illustration of a nondestructive inspection unit with a support structure in a second configuration in accordance with an illustrative embodiment.

Turning now to FIG. 8, an illustration of a nondestructive inspection unit with a support structure in a second configuration is depicted in accordance with an illustrative embodiment. In this illustrative example, support structure 702 is in second configuration 800.

As depicted, moveable section 710 has been moved in the direction of arrow 802. In this illustrative example, this movement is a combination of rotational and translational movement facilitated by rotation of link 712 in response to a manipulation of cable 715. In this example, link 712 rotates 180 degrees about hinge 722 in the direction of arrow 804 and moveable section 710 may rotate an additional 180 degrees about hinge 724 in the direction of arrow 804, for a total rotation of moveable section 710 by 360 degrees relative to support structure 702. This rotation results in a translation of eddy current sensor 706 and moveable section 710 in the direction of arrow 802 away from axis 718. In this illustrative example, the motion of cable 715 is a twisting type of motion instead of the pulling type of motion shown in the FIG. 3 and FIG. 4.

In second configuration 800, eddy current sensor 706 may generate data when performing an inspection. Borescope 704 is not obscured in this configuration. As a result, borescope 704 may generate an image that may be used to direct movement of eddy current sensor 706 to an area for performing the inspection.

When the inspection is completed, support structure 702 may be returned to first configuration 716 as seen in FIG. 7. In first configuration 716, support structure 702 may be moved back through an opening.

Figure 9:
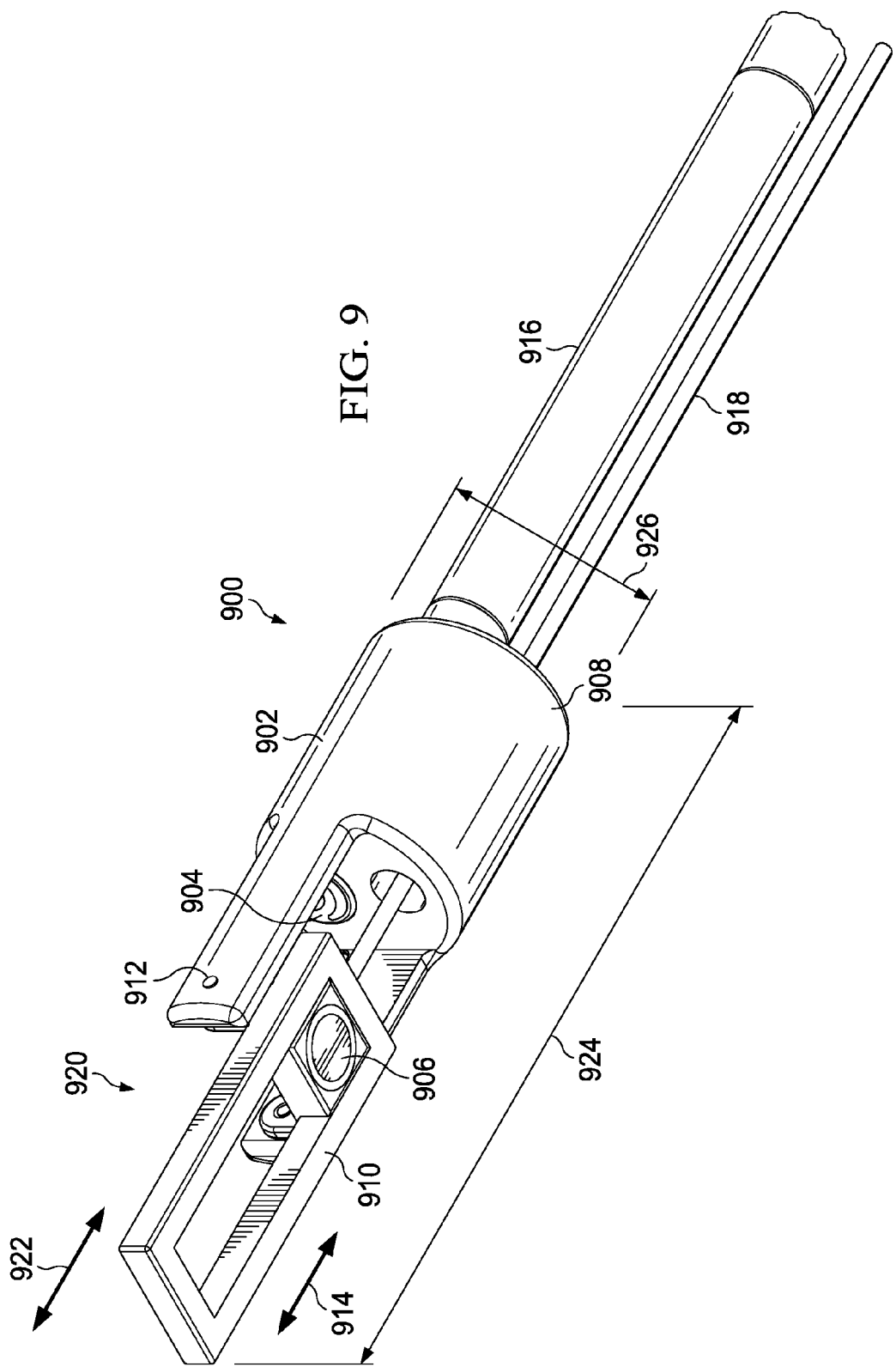
FIG. 9 is an illustration of a nondestructive inspection unit with a support structure in a first configuration in accordance with an illustrative embodiment.

Turning now to FIG. 9, an illustration of a nondestructive inspection unit with a support structure in a first configuration is depicted in accordance with an illustrative embodiment. In this illustrative example, nondestructive inspection unit 900 is another example of nondestructive inspection unit 208 shown in block form in FIG. 2.

As depicted, nondestructive inspection unit 900 includes support structure 902, borescope 904, and eddy current sensor 906. Borescope 904 is an example of an implementation for first sensor 216 shown in block form in FIG. 2. Eddy current sensor 906 is an example of an implementation for second sensor 218 shown in block form in FIG. 2. Support structure 902 is physically associated with borescope 904 and eddy current sensor 906.

In this illustrative example, support structure 902 includes base section 908 and moveable section 910. Borescope 904 is physically associated with base section 908 and eddy current sensor 906 is physically associated with moveable section 910. Base section 908 and moveable section 910 are connected to each other by hinge 912. In this illustrative example, hinge 912 is an example of an implementation for connector system 234 shown in block form in FIG. 2.

With hinge 912, moveable section 910 may rotate relative to base section 908. Additionally, moveable section 910 takes the form of a frame in this illustrative example. As depicted, eddy current sensor 906 also may move along moveable section 910 in the direction of arrow 914.

As depicted, base section 908 is connected to elongate structure 916. Additionally, cable 918 is also present. Cable 918 is connected to eddy current sensor 906 in this illustrative example. Manipulation of cable 918 may cause rotation of moveable section 910, movement of eddy current sensor 906, or some combination of the two.

As depicted, support structure 902 is in first configuration 920. In this configuration of support structure 902, borescope 904 is positioned in line with axis 922 extending through support structure 902 and, in particular, through base section 908 in support structure 902. Moveable section 910 holding eddy current sensor 906 is positioned parallel to axis 922 in this illustrative example. In this example, eddy current sensor 906 and borescope 904 are not in line with each other.

As depicted, this position of eddy current sensor 906 relative to borescope 904 may not be a desired position for performing eddy current testing. First configuration 920 is used when nondestructive inspection unit 900 is moved through an opening in this illustrative example.

Support structure 902 is moved out of first configuration 920 to perform an inspection. This movement out of first configuration 920 may be performed by manipulating cable 918.

In this illustrative example, support structure 902 may have length 924 and diameter 926. In this illustrative example, length 924 may be about 1.0 inch and diameter 926 may be about 0.35 inches. Of course, these values may vary depending on the particular implementation.

Figure 10:
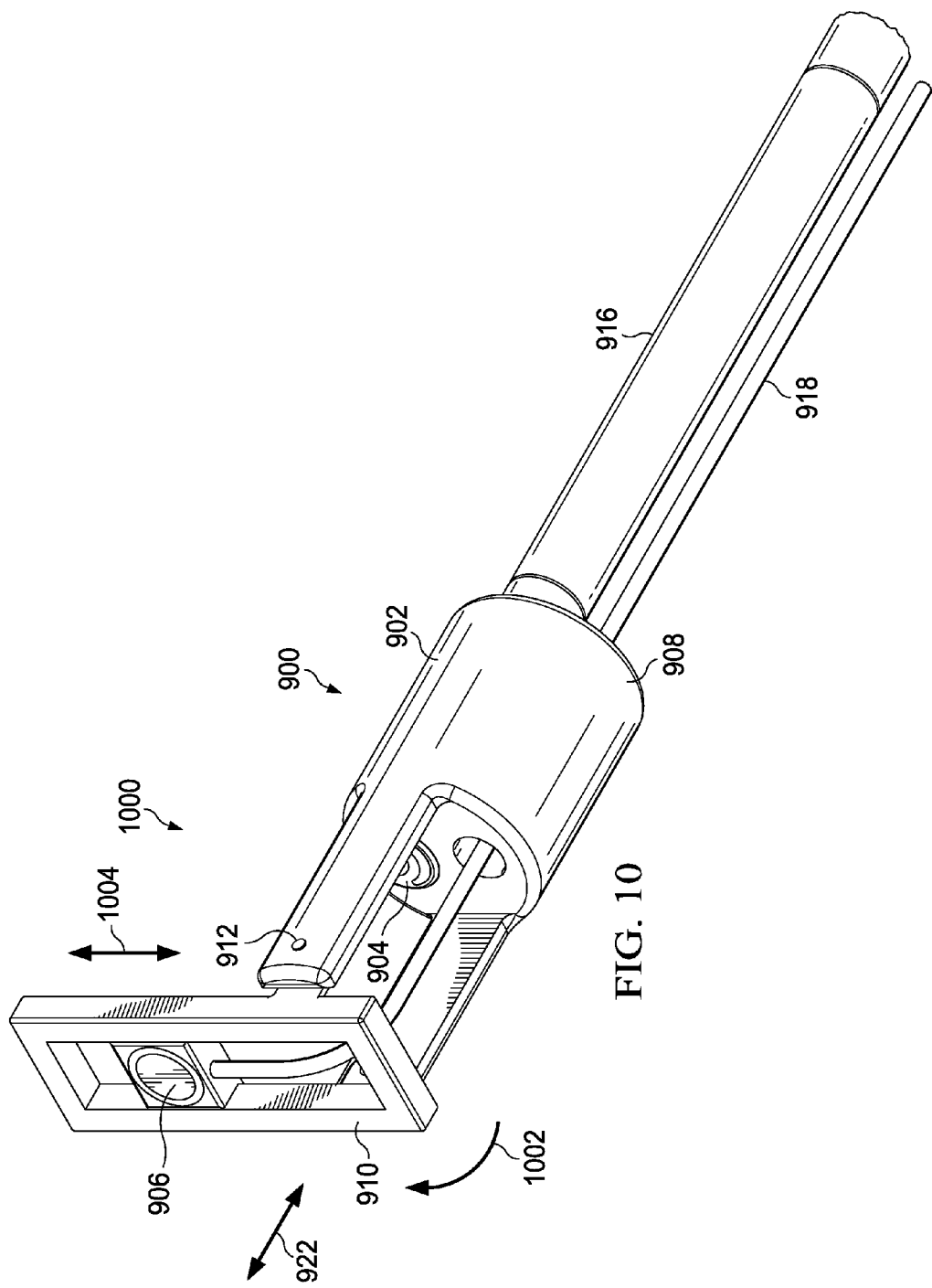
FIG. 10 is an illustration of a nondestructive inspection unit with a support structure in a second configuration in accordance with an illustrative embodiment.

With reference now to FIG. 10, an illustration of a nondestructive inspection unit with a support structure in a second configuration is depicted in accordance with an illustrative embodiment. In this illustrative example, nondestructive inspection unit 900 is another example of nondestructive inspection unit 208 shown in block form in FIG. 2.

In this illustrative example, support structure 902 is in second configuration 1000. As can be seen, moveable section 910 has been rotated in the direction of arrow 1002. In second configuration 1000, eddy current sensor 906 may be moved along moveable section 910 in the direction of arrow 1004. This movement may be used to position eddy current sensor 906 for performing eddy current testing.

For example, movement along moveable section 910 in the direction of arrow 1004 may be used to move eddy current sensor 906 over a line or crack when an inconsistency may be identified from a visual inspection using borescope 904. The eddy current testing may be used to generate more information about the inconsistency for analysis. In this manner, less movement of support structure 902 may be needed.

This configuration of support structure 902 may be useful when an inconsistency may be close to an opening through which support structure 902 is inserted for performing an inspection.

The illustrations of nondestructive inspection unit 300 in FIG. 3, nondestructive inspection unit 500 in FIG. 5, nondestructive inspection unit 700 in FIG. 7, and nondestructive inspection unit 900 in FIG. 9 have been presented only as examples of some implementations for nondestructive inspection unit 208 shown in block form in FIG. 2. These illustrations are not meant to limit the manner in which other illustrative embodiments may be implemented.

For example, additional linkage systems and moveable sections with additional sensors may be added to nondestructive inspection unit 300 in FIG. 3. Further, one or more additional rotating connectors may be used in addition to rotating connector 512 between moveable section 510 and base section 508 in FIG. 5. In this manner, difficult to access locations may be more easily reached using support structure 502.

The different components shown in FIG. 1 and FIGS. 3-10 may be combined with components in FIG. 2, used with components in FIG. 2, or a combination of the two. Additionally, some of the components in FIG. 1 and FIGS. 3-10 may be illustrative examples of how components shown in block form in FIG. 2 can be implemented as physical structures.

Figure 11:
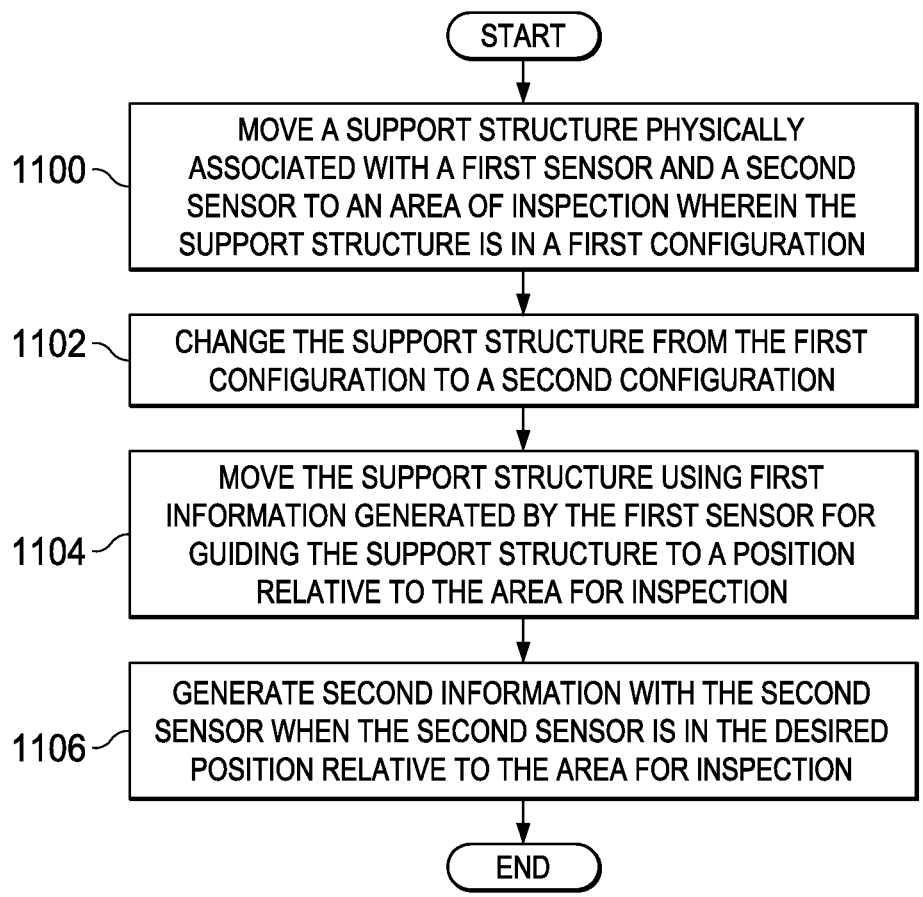
FIG. 11 is an illustration of a flowchart of a process for inspecting an object in accordance with an illustrative embodiment.

With, reference now to FIG. 11, an illustration of a flowchart of a process for inspecting an objet is depicted in accordance with an illustrative embodiment. In this illustrative example, the process depicted in FIG. 11 may be implemented in inspection environment 200 using nondestructive inspection system 204 shown in block form in FIG. 2.

The process begins by moving a support structure physically associated with a first sensor and second sensor to an area of inspection wherein the support structure is in a first configuration (operation 1100). The process then changes the support structure from the first configuration to a second configuration (operation 1102).

The process then moves the support structure using first information generated by the first sensor for guiding the support structure to a position relative to the area for inspection (operation 1104). In operation. 1104, the support is in the second configuration as the support structure is moved to the position. The process then generates second information with the second sensor when the second sensor is in the desired position relative to the area for inspection (operation 1106), with the process terminating thereafter.

Of course, other operations (not shown in this figure) may be performed prior to the process terminating. For example, the support structure may be moved, to one or more other positions to generate additional second information. As another example, the support structure may be changed back to the first configuration and removed from the area.

In this manner, the first sensor may be used to guide movement of the support structure to generate information for analysis using the second sensor. With a support structure that changes between a first configuration and a second configuration, the support structure may be moved to the area though an opening in the second configuration and used to generate information as desired.

With reference now to FIG. 12, an illustration of a flowchart of a process for inspecting a difficult to access area is depicted in accordance with an illustrative embodiment. The process illustrated in FIG. 12 may be implemented using nondestructive inspection unit 208 shown in block form in FIG. 2. For example, this process may be used to inspect interior 113 under cargo floor panel 102 in aircraft 103 in FIG. 1.

The process begins by identifying an opening to an area for inspection (operation 1200). A nondestructive inspection unit with a support structure in a first configuration is inserted through the opening into the area (operation 1202). The process then changes the configuration of the support structure from the first configuration to a second configuration (operation 1204).

A visual inspection is performed in the area using a first sensor in the nondestructive inspection unit (operation 1206). In this illustrative example, this first sensor may be a sensor that generates a view of the area for the operator.

A determination is made as to whether an inconsistency is identified using the visual inspection (operation 1208). If an inconsistency is identified, a second sensor is positioned relative to the inconsistency to generate data about the inconsistency (operation 1210). The second sensor may be positioned using the view of the inconsistency generated by the first sensor.

The process then generates data about the inconsistency (operation 1212). This data may be analyzed to obtain more information about the inconsistency. This additional information may include the depth of the inconsistency, the shape of the inconsistency, the size of the inconsistency, and other suitable types of information that may not be apparent from a visual inspection. For example, the depth of the inconsistency may not be determined through a visual inspection of the surface. Further, the size of the inconsistency may be greater than what is shown in the surface through the visual inspection.

Next, a determination is made as to whether the inspection has been completed (operation 1214). If the inspection has been completed, the support structure is placed into the first configuration (operation 1216). The nondestructive inspection unit is then removed from the area back through the opening (operation 1218).

The data about the inconsistency is then analyzed (operation 1220). An action is then identified based on the analysis of the data (operation 1222), with the process terminating thereafter. In these illustrative examples, this action may take various forms. For example, the action may be to perform rework, replacement of a part, increased inspection, or other suitable actions.

With reference again to operation 1214, if the inspection has not been completed, the process returns to operation 1206. Additionally, the process proceeds to operation 1214 from operation 1208 if an inconsistency is not identified. At this point, the nondestructive inspection unit may be moved to continue inspecting the area.

Illustrative embodiments of the disclosure may be described in the context of aircraft manufacturing and service method 1300 as shown in FIG. 13 and aircraft 1400 as shown in FIG. 14. Turning first to FIG. 13, an illustration of an aircraft manufacturing and service method is depicted in the form of a block diagram in accordance with an illustrative embodiment. During pre-production, aircraft manufacturing and service method 1300 may include specification and design 1302 of aircraft 1400 in FIG. 14 and material procurement 1304.

During production, component and subassembly manufacturing 1306 and system integration 1308 of aircraft 1400 in FIG. 14 takes place. Thereafter, aircraft 1400 in FIG. 14 may go through certification and delivery 1310 in order to be placed in service 1312. While in service 1312 by a customer, aircraft 1400 in FIG. 14 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of an aircraft is depicted in the form of a block diagram in which an illustrative embodiment may be implemented. In this example, aircraft 1400 is produced by aircraft manufacturing and service method 1300 in FIG. 13 and may include airframe 1402 with plurality of systems 1404 and interior 1406. Examples of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. For example, an illustrative embodiment may be used to perform inspections of structures for aircraft 1400 during component and subassembly manufacturing 1306. Additionally, inspections of structures for aircraft 1400 may be inspected during certification and delivery 1310. Additionally, inspections may be performed using an illustrative embodiment during maintenance and service 1312. The use of a number of the different illustrative embodiments may substantially expedite the assembly of and/or reduce the cost of aircraft 1400.

Thus, the illustrative embodiments provide a method and apparatus for inspecting objects. An inspection unit implemented in accordance with an illustrative embodiment may provide an ability to both perform a visual inspection and to generate information for analysis. The visual inspection may be performed to identify inconsistencies for which additional information may be desired. In these illustrative examples, the visual inspection is performed using a first sensor and the additional information may be generated using a second sensor, both of which are physically associated with the support structure as described above.

The support structure has a first configuration that allows for insertion of the nondestructive inspection unit through an opening such as a fastener hole. In this manner, more than one hole is not needed to perform a visual inspection and to guide the second sensor towards an inconsistency to generate more information about the inconsistency for analysis.

In the illustrative examples, the use of the nondestructive inspection unit reduces a need for disassembly of parts in an object. In this manner, inspections may be made more easily, resulting in less cost and time needed for inspections of an object such as an aircraft. This type of nondestructive inspection may be implemented for surgical nondestructive inspection when openings such as axis holes are smaller than desired for currently available nondestructive inspection units.

With the use of a nondestructive inspection unit, such as nondestructive inspection unit 208 shown in block form in FIG. 2, inspection of limited access areas in an aircraft as well as other objects may be performed with reduced disassembly of parts in the aircraft. Further, with the use of nondestructive inspection unit 208, misidentification of inconsistencies and false alerts that occur with only visual inspections may be reduced. In other words, visual inspections may identify inconsistencies that may require disassembly of parts to perform additional testing to generate data to analyze the inconsistency identified through the visual inspection. As a result, unnecessary disassembly of parts and increased costs may be reduced.

With nondestructive inspection unit 208, a visual inspection may be followed up with the generation of data about an inconsistency identified through the visual inspection. With nondestructive inspection unit 208, this data may be generated without disassembly of parts to generate the additional data about an inconsistency.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a first sensor;
a support structure that comprises a base section, a connector system, and a moveable section that comprises a tool, the moveable section biased by a spring connected to the moveable section and to the base section, such that a central axis of the tool aligns with a central axis of the first sensor and a central axis of the support structure in a first configuration;
a cable connected to the moveable section, the cable configured such that in operation, a manipulation of the cable overcomes a bias from the spring and moves the moveable section relative to the base section; and
the support structure physically associated with the first sensor and the tool such that the support structure comprises a configuration that in operation changes between the first configuration and a second configuration that comprises the central axis of the tool misaligned from the central axis of the first sensor, such that in operation in the first configuration, the support structure moves through an opening in an object.

2. The apparatus of claim 1 further comprising:
a movement system that comprises the cable and configured such that in operation, the movement system moves the support structure between the first configuration and the second configuration.

3. The apparatus of claim 1, further comprising the second configuration comprising the first sensor and the second tool configured relative to each other such that in operation, the apparatus generates information in a desired manner.

4. The apparatus of claim 1, wherein first configuration comprises the first sensor and the tool each positioned about an axis that extends through the support structure.

5. The apparatus of claim 4, further comprising the first configuration configured such that the tool is located in front of the first sensor and wherein the second configuration comprising the tool configured away from the axis and out from in front of the first sensor.

6. The apparatus of claim 1, further comprising:
the first sensor physically associated with the base section; and
the connector system connected to the base section and the moveable section, wherein the moveable section is configured to move relative to the base section such that in operation the tool moves relative to the first sensor as the support structure changes between the first configuration and the second configuration.

7. The apparatus of claim 6, wherein the connector system is a linkage system.

8. The apparatus of claim 1, wherein the first sensor is selected from one of a camera, a video imaging system, and a borescope.

9. The apparatus of claim 1, wherein the tool comprises one of: an eddy current sensor, an ultrasonic transducer, a chemical sensor, a biological sensor, an infrared sensor, a thermocouple temperature sensor, a magnetic field sensor, a vibration sensor, an electrical potential sensor, an electrostatic discharge sensor, a marking instrument, a light, a pen, a marker, a sealant applicator, and a paint applicator.

10. The apparatus of claim 1, further comprising a group that comprises: a second sensor, a marking instrument, a light, a pen, a marker, a sealant applicator, a paint applicator, each member of the group configured as a module that forms the tool in a modular configuration that interchangeably connects to and detaches from the moveable section.

11. The apparatus of claim 1, wherein the sensor, the tool, and the support structure with the support structure in the first configuration are configured to be moved through a fastener hole.

12. The apparatus of claim 1, wherein the object is selected from one of a mobile platform, a stationary platform, a land-based structure, an aquatic-based structure, a space-based structure, a deformable structure, a flexible fuel bag, a fuel line, a surface ship, a tank, a personnel carrier, a train, a spacecraft, a space station, a satellite, a submarine, an automobile, a power plant, a bridge, a dam, a house, a manufacturing facility, a building, an aircraft wing, a fairing, a fuel tank, a fuselage, an engine, and a duct system.

13. A nondestructive inspection system that comprises: an imaging sensor; a support structure that comprises a base section and a moveable section connected by a rotating connector connected to a cable; the support structure physically associated with the imaging sensor and a tool, such that the support structure comprises a first configuration that comprises the imaging sensor and the tool positioned about an axis that extends through the support structure; the support structure is further configured such that in operation, a twist of the cable changes the support structure between the first configuration and a second configuration, such that the support structure, in the first configuration, moves through an opening in a structure; and the second configuration comprises the imaging sensor and the tool each positioned to perform a desired function.

14. The nondestructive inspection system of claim 13, wherein the imaging sensor and the tool are positioned about the axis extending through the support structure; the tool is located in front of the imaging sensor when the support structure is in the first configuration; and the tool is configured to move away from the axis when the support structure changes from the first configuration to the second configuration.

15. The nondestructive inspection system of claim 13, further comprising:
   the imaging sensor physically associated with the base section; and
   the moveable section configured such that in operation the moveable section moves relative to the base section such that the tool moves relative to the imaging sensor as the support structure changes between the first configuration and the second configuration.

16. The nondestructive inspection system of claim 15, further comprising:
   the cable configured in a twistable manner, such that in operation twisting the cable moves the moveable section relative to the base section via rotating the rotating connector; and
   a group that comprises: a second sensor, a marking instrument, a light, a pen, a marker, a sealant applicator, a paint applicator, each member of the group configured as a module that forms the tool in a modular configuration that interchangeably connects to and detaches from the moveable section.

17. A method for inspecting an object, the method comprising: connecting a cable to a pin in a first hinge in a link, the link connected to a base section, of an inspection unit, the base section comprising a first sensor, the link forming a hemisphere of an exterior of the base section in a first configuration of the inspection unit; connecting the pin an moveable section of the inspection unit, the moveable section comprising a tool: moving the inspection unit to an area for inspection, the inspection unit being in the first configuration comprising the first sensor and the tool positioned about an axis extending through the base section; and changing the inspection unit from the first configuration comprising the first sensor and the tool configured for performing a desired function via separating the first sensor and the tool, thereby misaligning a central axis of the first sensor from a central axis of the tool, via rotating, about a second hinge, the link away from the base section.

18. The method of claim 17 further comprising:
   moving the inspection unit in the second configuration using first information generated by the first sensor for guiding the tool to a desired position relative to the area for the inspection;
   configuring the tool as a module, the tool comprising a selection from a group comprising: a second sensor, a marking instrument, a light, a pen, a marker, a sealant applicator, a paint applicator, configuring each member of the group modularly to interchangeably connect and detach from the moveable section; and
   generating second information from the tool being in the desired position relative to the area for inspection.

19. The method of claim 17, wherein moving the inspection unit to the area for inspection comprises:
   moving the inspection unit in the first configuration through an opening to the area for inspection, such that the first configuration comprises the first sensor and the tool aligned along the axis extending through the base section.

20. The method of claim 17, further comprising:
   a connector system comprising the link connected to the base section and the moveable section and moving the moveable section relative to the base section via moving the pin along a length of the base section and rotating the moveable section away from the base section via rotating the link via twisting the cable and thus changing the inspection unit between the first configuration and the second configuration.

* * * * *